United States Patent [19]
Pullen et al.

[11] Patent Number: 5,723,306
[45] Date of Patent: Mar. 3, 1998

[54] MONOCLONAL ANTIBODIES FOR THE DETECTION OF PYRETHROIDS AND A PROCESS FOR THEIR PRODUCTION

[75] Inventors: Sabine Pullen; Berthold Hock, both of Freising; Thomas Wuske, Malente; Andreas Manns, Lubeck, all of Germany

[73] Assignee: Dragerwerk Aktiengesellschaft, Lubeck, Germany

[21] Appl. No.: 296,050

[22] Filed: Aug. 24, 1994

[30] Foreign Application Priority Data

Sep. 4, 1993 [DE] Germany .................. 43 29 952.0

[51] Int. Cl.$^6$ .................. G01N 33/577; C07K 16/44; C12N 5/24
[52] U.S. Cl. .................. 435/7.93; 435/7.5; 435/172.2; 435/240.27; 530/388.9
[58] Field of Search .................. 530/388.9; 435/240.27, 435/172.2, 7.5, 7.93

[56] References Cited

FOREIGN PATENT DOCUMENTS 327163  9/1989  European Pat. Off. .

OTHER PUBLICATIONS

J. Skerritt et al., ACS Symp. Ser., 451 (Immunoassays Trace Chem. Anal., pp. 124–138 (1990).

J. Skerritt et al., J. Agric. Food Chem., vol. 40, pp. 1287–1292 (1992).

L Stanker et al., J. Agric. Food Chem., vol. 37, pates 834–839 (1989).

S. Pullen et al., Analytical Letters, vol. 28, No. 5, pp. 765–779 (1995).

Goodfriend, T.L., Levine, L. & Fasman, G.D. (1964); Antibodies to bardykinin and Angiotensin; a use of Carbodimides in immunology, Science 144, 1344–1346.

Harlow, E. & Lane, D., Hrsg., (1988) Antibodies, a laboratory manual, Cold Spring Harbor Lab., Cold Spring Harbor, USA, pp. 141–243.

Burrin, J. & Newman, D. (1992): "Production and assessment of antibodies"; In: Principles and practice of immunoassay, (Price, C.P. & Newman, D. Hrsg.), Stockton press, New York, USA, pp. 19–52.

Campbell, A.M., (1991): "Monoclonal antibody and immunsensor technology"; Laboratory techniques in biochemistry and molecular biology, 23, (van der Vliet, P.C., Hrsg.) Elsevier science publishers B.V., Amsterdam, NL, pp. 1–49. Leahey, J.P. Hrsg., (1985): The Pyrethroid Insecticides, Taylor & Francis Ltd. London UK, pp. 11–33.

Märtlbauer, E. & Terplan, G. (1987): Ein enzymimmunologischer Nachweis von Chloramphenicol in Milch, Archiv f. Lebensmittelhygiene, 38, 1–7.

Rodbard, D. (1978): Data processing for radioimmunoassay: an overview., in: Clinical Immunoassay: cellular basis and applications in disease. (Natelson, Pesce & Dietz., Hrsg.). Am. Assoc. for Clin. Chem., Washington DC, 477–494.

Rodgers, R.P. C. (1984): Data analysis and quality control of assays: a practical primer, in: Practical Immunoassay, the state of the art (Butt, W.R. Hrsg.), Dekker–Verlag, New York, 253–308.

Stocker, J. W. et al. (1982): Generation of 2 new mouse myeloma cell lines "PAI and PAI–O" for hybridoma production. Hoffmann–La Roche Research Disclosure, 21713, 155–157.

Tijssen, P. (1985): Practice and Theory of Enzyme Immunoassays (Burdon, R. H. & Knippenberg, P.H., Hrsg.), Elsevier, Oxford, UK, pp. 221–296.

Van Emon, J. M. & Mumma, R.O. Hrsg., (1990): Immunochemical Methods for Environmental Analysis, ACS symposium series 442, ACS Washington, USA, pp. 51–57, 156–167, 180–210.

Wing, K.D., Hammock, B.D. & Wustner, D.A. (1978): Development of an SBioallethrin specific antibody, J. Agric. Food chem., 26, 1328–1333.

PCT WO 90/10450: Monoclonal Antibodies to Synthetic Pyrethroids and Methods for Detecting the Same, Sep. 20, 1990.

European Patent No. 235,000 A1: Iodine–Marked Pyrethroids, Process and Intermediates for their Preparation, and their Application to Radioimmunoassays, Sep. 2, 1987.

European Patent No. 365,818 A1: Immunological Detection of Atrazine and Atrazine Derivatives.

*Primary Examiner*—Mary E. Ceperley
*Attorney, Agent, or Firm*—Caesar, Rivise, Bernstein, Cohen & Pokotilow, Ltd.

[57] ABSTRACT

Highly selective monoclonal antibodies for pyrethrins and pyrethroids which, in their function as pesticides, contain a phenoxybenzyl and/or a cyclopropane component. The number of pyrethroids which can be selectively detected is increased and the possibility of differentiating among the various pyrethrins, pyrethroids and their metabolites is possible. An easy-to-use test kit detects pyrethrins and pyrethroids.

A conjugate of a metabolite of the pyrethrins/pyrethroids (especially permethric acid or phenoxybenzoic acid) is coupled as hapten to a carrier protein to obtain the immunogen, which is used for immunization and for the subsequent cloning of suitable hybridomas.

18 Claims, 7 Drawing Sheets

PYRETHROID-MIX I   PYRETHROID-MIX II

ALLETHRIN

PYRETHRINE (a)

FENFLUTHRIN

PERMETHRIN  PERMETHRIN

CYPERMETHRIN  CYPERMETHRIN

CYFLUTHRIN

DELTAMETHRIN

FIG. 8   FENVALERAT

MONOCLONAL ANTIBODIES FOR THE DETECTION OF PYRETHROIDS AND A PROCESS FOR THEIR PRODUCTION

RELATED APPLICATIONS

On Sep. 4, 1993, the assignee of the present invention, Dr ägerwerk Aktiengesellschaft of 23542 Lübeck, Federal Republic of Germany, submitted a patent application in the Federal Republic of Germany, on the present invention entitled Monoclonal Antibodies for the Detection of Pyrethroids and a Process for their Production, File No.: P 4,329,952.0, of which Applicants claim priority under 35 U.S.C. § 119.

BACKGROUND OF THE INVENTION

The invention pertains to monoclonal antibodies which have a high specificity to, and affinity for, an insecticidal or pesticidal active ingredient from the group of the pyrethrins and pyrethroids and their derivatives which, in their function as pesticides, contain a phenoxybenzyl and/or a cyclopropane component. The invention also pertains to a process for the production of monoclonal antibodies in which a conjugate consisting of a hapten and an immunogenic carrier is used as the immunogen and to a test kit for carrying out an immunoassay with the use of the monoclonal antibodies.

The intensification and specialization of agriculture are no longer imaginable without the use of plant protection agents (pesticides, i.e., herbicides, insecticides, fungicides). Studies have shown, however, that plant protection agents and their decomposition products (metabolites) not only remain after their application in the upper layers of the soil but also find their way into the groundwater and bodies of surface water. The environmental burdens associated with this have recently become the focus of repeated public discussion. Pesticides must contain biologically active ingredients to achieve their intended effects (insecticide, antifeeding effect). Danger to the health of human beings and to the environment can be linked with their use. For this reason, lawgivers have defined limit values for pesticides, including their main toxic decomposition products, in, for example, drinking water, food products, and at the work place (MWO=maximum work place concentration).

Pyrethrum is the oldest known insecticide obtained from plants, and it is actually a mixture of various insecticidal substances, the so-called "pyrethrins." In view of the toxicologic and ecologic reservations against, for example, insecticidal phosphoric acid esters, chlorinated hydrocarbons (lindane, POP, DDT, toxaphene) and carbamates, pyrethrins offer an extremely interesting group of highly valuable, desirable properties for use as insecticides. Naumann, K., (1981): Chemie der synthetischen Pyrethroidinsektizide, Band 7: Chemie der Pflanzenschutz - und Sch ädlingsbekämpfungsmittel, (Wegler, R., Hrsg.), Springer-Verlag, Berlin, Heidelberg, BRD. This is reflected in the continuously increasing market share of pyrethrin-containing agents. It is widely considered a non poisonous agent which is compatible with nature, but in no way is it considered to be without problems. Pyrethrum has been categorized as slightly to moderately toxic to mammals. Human beings in regular contact with pyrethrum can develop pathologic skin reactions. Stabilizers and synergists are added to pyrethrum to delay its decomposition and metabolism, but this prolongs the persistence of the substance in nature. Insects, fish, and other creatures of economic importance are exposed to the substance for a longer period of time. Because the bodies of mammals can be penetrated more quickly and because mammal metabolism proceeds more slowly, the toxicity of the substance is greater and therefore the potential for endangerment is higher.

The pyrethroids are produced synthetically in imitation of natural pyrethrins to be more toxic to insects, more persistent (more active as residues), and therefore more effective as insecticides. Naumann, supra; Leahey, J. P. Hrsg., (1985): The Pyrethroid Insecticides, Taylor & Francis Ltd. London UK. More than 100 pyrethroids are known today. In some cases, their structure and/or their activity bear only slight resemblance to those of their natural counterparts. Pyrethroids, however, also have undesirable effects on human beings and other creatures. In addition, they have a bioaccumulation potential, i.e., their accumulation in fatty tissue, in aquatic organisms, and in plants indicates a buildup in the food chain. This can lead to chronic toxic effects in the human brain. The half-life of pyrethroids in the soil, for example, varies as a function of the type of active ingredient, the formulation, and the type of soil, but in general it is between 1 week and 60 weeks. In addition, both the pyrethroids and the pyrethrins are nonselective with respect to insects (toxic to bees) and are highly toxic to fish.

For the reasons outlined above, it must therefore be considered an urgent task to improve the existing methods for detecting pyrethrins and synthetic pyrethroids and their decomposition products (metabolites). It would be especially desirable to develop low-cost, efficient, and easy-to-perform methods which can also be applied outside the laboratory under field conditions or at home and which give the farmer, analyst, ecologist, allergy specialist, physician, and other users quick and reliable information on whether and in what concentration range a certain active ingredient or metabolite is present in, for example, food, air, soil, or water. It was therefore the task of the present invention to provide a detection system for insecticides or pesticides which is reproducible, low in cost, simple to perform, applicable on-site, and quick to evaluate.

The current standard physical-chemical analysis methods (TLC=thin-layer chromatography; HPLC=high-performance liquid chromatography; GC=gas chromatography; GC-MS=GC-mass spectrometry) for pyrethrins and pyrethroids require complicated enrichment procedures, are expensive and time-consuming, and can be conducted only by specially trained technicians in extremely well-equipped laboratories. For example, for the determination of pyrethroids in soil samples by means of HPLC, it is necessary, before the performance of the actual chromatographic analysis, to carry out complicated intermediate purification and concentration steps. Because of the low vapor pressure of these compounds, GC-MS analysis requires a great deal of effort to perform. To avoid these disadvantages, methods (immunoassays) have been recently developed like those that are used routinely in clinical diagnostics for the detection of a wide variety of substances, especially for the quantitative and qualitative determination of pollutants in samples of foods products, soil, water, and air. For example, work has already begun on the development of immunological methods for the detection of certain herbicides and pesticides. Van Emon, J. M. & Mumma, R. O. Hrsg., (1990): Immunochemical Methods for Environmental Analysis, ACS Symposium Series 442, ACS Washington, USA. Methods have also already been described for the immunologic detection of pyrethroids (Wing, K. D., Hammock, B. D. & Wustner, D. A. (1978): Development of an SBioallethrin specific antibody, J. Agric. Food Chem., 26, 1328–1333); but, like most other pesticide immunoassays, these methods are based on the use of polyclonal antisera. This is the point at which the present invention intervenes, inasmuch as it takes on the additional goal of providing monoclonal antibodies and the mouse hybridoma cell lines to produce these antibodies, which, in conjunction with an immunologic method and a test unit, are suitable for the simple, specific, and sensitive detection of pyrethroids and/or pyrethrins and their metabolites. The goal is to provide a detection method which is standardizable and reproducible, requires little in the way of technical and material effort, and offers the possibility of rapid qualitative and quantitative pesticide determinations.

Immunoassays are highly sensitive and selective serological analysis methods for the qualitative/quantitative determination of substances on the basis of the immunologic antibody-antigen reaction. In immunoassays (IAs), a component of the immune reaction, i.e., either the antigen (hapten) or the antibody, is coupled with an easy-to-detect marker substance. The radioimmunoassay (RIA), the fluorescence immunoassay (FIA), and the enzyme immunoassay (EIA) have all been found useful. European Patent No. A-235,000 describes the possibility of radioactively labeling pyrethroids to serve as analytes or tracers for RIAs. Other pyrethroid RIA systems are described by Wing, supra.

Antibodies are induced by the immunization of laboratory animals and are then isolated by conventional methods. Harlow, E. & Lane, D., Hrsg., (1988) Antibodies, a laboratory manual, Cold Spring Harbor Lab., Cold Spring Harbor, USA. Substances (molecules) which induce a specific immune response and are able to react with the products of this immune response are referred to in the widest possible sense of the word as antigens. Molecules with a molecular weight of less than 10,000 daltons are usually weak immunogens. Molecules with a molecular weight of less than 2,000 daltons are almost incapable of inducing an immune response by themselves. They are called haptens. According to the state of the art, substances which are not antigenic (haptens) and against which antibodies are to be produced are bound to a high-molecular, usually soluble immunogenic molecule ("carrier") to form so-called conjugates, which are then used to immunize animals such as rabbits or mice. When immunization is carried out with hapten carrier conjugates, hapten-specific antibodies are not the only antibodies which are induced and formed; on the contrary, antibodies which are directed against the carrier, against the bonding component between the carrier and the hapten, or only against the entire complex made up of the hapten (bonding component) carrier are also produced. There are many established techniques for coupling haptens to carriers. Tijssen, P. (1985): Practice and Theory of Enzyme Immunoassays (Burdon, R. H. & Knippenberg, P. H., Hrsg.), Elsevier, Oxford, UK. The specific anti-hapten antibodies are usually directed against the part of the molecule which is the farthest away from the carrier.

In PCT WO 90/10.450 is described a complicated synthesis procedure. This complexity is required, because pyrethroids such as permethrin and phenothrin do not contain any functional groups which allow for a direct covalent coupling to a carrier protein. For this reason, the first step in PCT WO 90/10.450 is to synthesize the pyrethroid phenothrin and then to proceed from that to form a monoester of cyclopropanedicarboxylic acid of phenothrin. This latter compound has a free carboxyl group on the chrysanthemum acid component of the pyrethroid molecule, and this group can be used to form a covalent hapten-carrier bond with a primary amino group on the carrier protein. As a result, when antibodies bind to a hapten-carrier conjugate formed in this way, they bind to the part of the molecule which is farthest away, namely, the phenoxybenzyl part. Therefore, antibodies which are isolated on the basis of the known antigen tend to bind only to pyrethroids or their derivatives which have a phenoxybenzyl group as an epitope (antigen-like structural component). Pyrethroids without an epitope of this kind are not bound at all or are bound only loosely.

In EP 235,000 is disclosed an invention relating to the radioactive labeling of pyrethroids, more specifically to the $I^{125}$-labeling of pyrethroids. That disclosure states that it is to provide chemical procedures for the synthesis of pyrethroid-derivatives to be used as conjugated antigen or as radioactive labeled analytes or tracers for radioimmunoassays (RIA). That reference describes complicated synthetic procedures, labeling or protein coupling methods, product clean up and the final analysis of the pyrethroid-derivatives produced. This complexity is required because pyrethroids normally do not contain functional groups which allow for the direct coupling to other groups or chemicals (analogously described in PCT WO 90/10450). As exemplified in the disclosure, only synthetic pyrethroids which possess the phenoxybenzyl and cyclopropane functionalities are used. The synthetic pathway for the production of haptene-carrier protein linkage or radioactive labeling starts at the 3-phenoxybenzyl group of the pyrethroid-molecule. That disclosure does not pertain to a process for the production of monoclonal antibodies or for an immunoassay method and test kit. Claims 16-19 of that reference do disclose the application of the above described pyrethroid-derivatives, for use in hapten-carrier coupling reactions and immunization.

One distinction between the disclosure of PCT WO 90/10450 and EP 235,000 is that the synthetic pathway for the production of the hapten-carrier protein linkage of the pyrethroid molecules. Additionally, the PCT WO 90/10450 reference provides monoclonal antibodies and the hybridomas that produce these monoclonal antibodies which will react specifically and sensitively with synthetic pyrethroids. Further, PCT WO 90/10450 provides a method for the production of monoclonal antibodies and a method for detecting the separation of synthetic pyrethroids from samples.

To increase the number of detectable pyrethroids and simultaneously to achieve a higher specificity to pyrethroids with a structure which is dissimilar to that of the hapten (inasmuch as it is also desirable to be able to detect metabolites of the pyrethroids), the hapten bound to the immunogenic carrier is, according to the invention, a metabolite of the pyrethrins and/or pyrethroids. A "metabolite" in this context is understood to be a structural molecule or component which is needed for the synthesis of the pyrethroids or which forms during the metabolization of pyrethroids. Metabolites in this sense can be chemically or toxicologically different from the pyrethroids. It is therefore not necessary to limit the choice of immunization hapten to the pyrethroids or pyrethrum; on the contrary, it is now possible to use the two basic structural components of the pyrethroids or pyrethrins (the alcohol component and the acid component), separately from each other, for the hapten-carrier coupling, for the subsequent immunization, and for the screening and characterization of the induced/isolated antibodies. This opens up the possibility of the obtaining antibodies with high specificity to the pyrethroids or pyrethrins which contain only one of the components in their basic structure and of obtaining antibodies with high specificity to, for example, pesticide metabolites still containing at least one of these components as structural features.

It has been found that an excellent tracer for the detection of pyrethroids in an extremely wide variety of immunoassays can be obtained by bonding the basic structural components to an enzyme or to the strept-avidin biotin system as a carrier.

The use of individual structural components for the production of monoclonal antibodies opens up the possibility of isolating a "set" of different monoclonal antibodies, which, with respect to their immunologic binding, differ from the pyrethroids/pyrethrins and under certain conditions supplement them. In this way, it would be possible to produce a defined "cocktail" of monoclonal antibodies (similar to a polyclonal serum) with the high sensitivities (i.e., very low detection limits) characteristic of polyclonal antibody sera and a wider selectivity. At first glance; it appears illogical to mix monoclonal antibodies after taking the trouble to isolate them by complicated procedures. Nevertheless, monoclonal antibodies can be considered so-called "standardized reagents", whereas polyclonal antibody sera have an undesirable breadth of variation in the present context, as will be described further below. Because the contribution made by each individual antibody in the synthetic mixture is known, the cocktails produced from these antibodies can therefore be defined precisely. Burrin, J. & Newman, D. (1992): "Production and assessment of antibodies"; in: Principles and practice of immunoassay, (Price, C. P. & Newman, D. Hrsg.), Stockton Press, New York, USA. Through the combination ("pooling") of monoclonal antibodies with high affinities, it is possible in some cases to produce test systems or immunoassays with expanded detection limits. In cases where it is impossible to isolate monoclonal antibodies with high affinities, individual antibodies of weak-to-medium affinity can be combined to arrive at a defined "polyspecific antibody mixture" with preferred (higher) affinity to a certain antigen determinate. Campbell, A. M., (1991): "Monoclonal antibody and immunsensor technology"; Laboratory techniques in biochemistry and molecular biology, 2–3, (van der Vliet, P. C., Hrsg.) Elsevier Science Publishers B.V., Amsterdam, NL. In this way, the EIA properties can be controlled individually as a function of the specific requirements by adjusting the concentrations of the individual monoclonal antibodies.

Antibodies recognize the three-dimensional structure/conformation of an analyte and are therefore able to differentiate between optical isomers. In this respect, an immunoassay or immuno-affinity chromatography method offers the possibility of enriching specific structural isomers selectively and of identifying or separating them, a feat which is nearly impossible with the standard physical and chemical analysis methods. To isolate antibodies with the cited properties, the isomers of the pesticide acid component, i.e., cis-permethric acid and trans-permethric acid, and phenoxybenzoic acid were used for individual hapten-carrier couplings, and the hapten antigens thus formed were used for immunization.

Another advantage of the use of individual structural components as haptens (acid or alcohol component) for the formation of antigenic conjugates consists in the favorable property that the antibodies produced with these haptens can be used in the immunoassays which work on the so-called displacement principle, because it is necessary to achieve a certain affinity for the tracer and a different one for the analytes, both at the same high level of specificity.

The antibodies obtained by means of the known immunization processes have the same high specificity to, or selectivity for, both the structural components and the pesticide molecules or metabolites derived therefrom, but their affinities are different. As a result, during the reaction, the analyte (pyrethroid, pyrethrum, or one of their metabolites) can displace a marked tracer (e.g., individual derivatized structural components) from its bond with the specific antibodies. When structural components (acid component or alcohol component) are used during the immunization of the animals, the handling and consumption of pesticides is considerably reduced in the performance of the experiments and in the use of the detection kit. For this reason and for all the other reasons described above, it is preferable to use the basic structural components of the pyrethroids or pyrethrum, i.e., cis- and trans-permethric acids and phenoxybenzoic acid, as haptens for the immunization of experimental animals and for the subsequent production of polyclonal or monoclonal anti-pesticide antibodies. These therefore have a high specificity to, and a moderate-to-high affinity for, the active ingredients of pesticides//insecticides (e.g., pyrethrum, bioallethrin, allethrin, phenothrin, fenfluthrin), that is, especially pyrethrum and its derivatives/metabolites, especially the acid component (cyclopropanecarboxylic acid, permethric acid), and also for several pyrethroids which have these structural components. Antibodies are obtained which have essentially no cross-reactivity with the alcohol component (phenoxybenzyl alcohol) of some pyrethroids or with the metabolite itself or with pyrethroids which have no cyclopropanecarboxylic acid derivative as a structural component. Special features of the production of monoclonal antibodies by means of the hapten conjugates according to the invention are to be seen in that the hybridoma cell lines or clones or subclones thereof obtained by means of these conjugates produce or synthesize the corresponding antibodies and preferably tend to secrete them almost entirely into the surrounding medium.

Monoclonal antibodies (MABs) have by now been produced against a large number of antigens and are well established in the field of medical diagnostics in particular. The advantages of monoclonal antibodies over those obtained from the antisera of animals immunized in the conventional way are numerous:

(a) monoclonal antibodies can be obtained in large quantities and with a high degree of purity;

(b) the production of monoclonal antibodies is homogeneous with respect to antigen reactivity and does not change over the course of time;

(c) monoclonal antibody-producing hybridoma cell lines can be stored for years and even decades without loss of their specific properties; and (d) monoclonal antibodies are more suitable for use as standard reagents than polyclonal antisera, because the latter are negatively affected by a wide range of variation with respect to, for example, the removal of blood from the immunized animals, the continuity of availability of material for additional immunizations, and the limited life-span of the donor animals. The in-vitro cultivation of the hybridoma cells according to the invention is carried out in suitable culture media, especially in standardized culture media used generally such as Dulbecco's Modified Eagle Medium (DMEM), RPMI 1640, and CG medium, which can be supplemented if desired by the addition of mammalian sera such as fetal calf serum (FCS) or by growth-stimulating additives and trace elements.

The isolation of the monoclonal antibodies involves various workup and purification steps, which are known to the expert in the field and which include, for example, the use of chromatographic methods such as protein-A/protein-G chromatography. The term "derivatives" of monoclonal antibodies is used within the scope of the present invention to mean, for example, fragments of antibodies which still have the specificity and affinity for the tracers and analytes in question as well as antibodies which have been marked in different ways, as summarized by way of example in European Patent No. A-365,818. Also included are recombinant antibodies and antibody fragments such as those cloned, genetically engineered, or expressed by means of DNA recombination methods in heterologous organisms.

The antibodies obtained in this way are especially suitable for use in one of the standard immunoassays for the detection of pyrethroids or pyrethrins and/or their metabolites/ derivatives as well as for the differentiation among individual pyrethroids or pyrethrins and/or their metabolites/ derivatives in samples of soil, air, water, and food products; on surfaces; in household dust; and in other biological materials such as those used in medical diagnostics. The monoclonal antibodies can therefore be used in all the known immunoassays which are based on the specific bonding between an antigen and the corresponding monoclonal antibody. Preferably, however, they are used in competitive or noncompetitive EIA tests such as the flow-injection method (FIA) and/or immunochromatography (MIDA, see German Patent Application No. P 4.229,591.2).

The known test methods are packaged in the form of test kits for the qualitative and quantitative determination of pyrethrins and/or pyrethroids or their metabolites or decomposition products containing their structural components. In addition to the monoclonal antibodies and/or their derivatives according to the invention, the test kits can also contain other monoclonal or polyclonal antibodies or their derivatives and also other additives. Test kits which are based on one of the conventional immunoassays, but especially those based on a fluorescence immunoassay (FIA) or an enzyme immunoassay (EIA), are especially preferred within the scope of this invention.

Test kits which are based on an immunoassay (e.g., the ELISA test) for the immunological detection of pyrethrin/ pyrethroids can contain, for example, the following components:

(a) a suitable carrier material, which can be left uncoated or which can be coated with one of the immunoconjugates, tracers, or antibodies according to the invention or with an antibody conjugate;

(b) freeze-dried or concentrated solutions of one of the antibody/antibody conjugates according to the invention and/or a second enzyme-marked monoclonal or polyclonal antibody directed against the antigen to be determined or against an antibody which recognizes the antigen;

(c) an enzyme substrate in solid or dissolved form;

(d) the antigen (tracer or enzyme conjugate) in solid or dissolved form;

(e) buffering and washing solutions;

(f) additives to prevent, for example, nonspecific adsorption and aggregation; and (g) pipers, reaction vessels, reference standards, calibration curves, and color tables.

Carrier materials which can be used within the scope of the present invention comprise primarily insoluble, polymeric materials, selected from the group consisting of polystyrene, polypropylene, polyester, polyacrylonitrile, polyvinyl chloride, polyacrylamide, cellulose nitrate, crosslinked dextrans, fluorinated resins, agarose, crosslinked agarose, and polysaccharides. In addition, however, other materials are also conceivable, such as glass, glass fibers, metal, nylon mesh material or nylon membranes. The carrier materials cited above are intended to serve as illustrations of the present invention and are not limiting. The carrier materials previously cited in detail can be in various shapes and can be designed in very different ways according to the purpose for which they are to be used. These forms include, for example, shells, spheres, plates, rods, strips, cells, small bottles, tubes, columns, fibers, mesh, and non-woven materials. So-called "microtiter plates" or reagent vessels of transparent plastic material, which can be either uncoated or coated with one of the antibodies according to the invention, with a free antigen, or with an antigen conjugate, are frequently used in the production of test kits. Furthermore, color-producing or signal-generating markers or indicators also form a component of the test kit; by means of these markers or indicators, it is possible to detect the presence of a complex-forming reaction, especially an immune reaction, which preferably leads to an antigen-antibody complex or to a ligand-receptor complex, as a result of which, in addition to qualitative conclusions, it may also be possible to arrive at quantitative conclusions concerning the antigen to be detected. Both individual atoms and molecules which either directly or indirectly participate in the production of a detectable signal and which are described by way of example in European Patent No. A-365,818 can be used as markers or indicators.

The invention is explained in greater detail below on the basis of exemplary embodiments and is illustrated in the associated figures.

SUMMARY OF THE INVENTION

These and other objects of this invention are achieved by providing highly selective monoclonal antibodies for pyrethrins and pyrethroids which, in their function as pesticides, contain a phenoxybenzyl and/or a cyclopropane component. The number of pyrethroids which can be selectively detected is increased and the possibility of differentiating among the various pyrethrins, pyrethroids and their metabolites is possible. An easy-to-use test kit detects pyrethrins and pyrethroids.

A conjugate of a metabolite of the pyrethrins/pyrethroids (especially permethric acid or phenoxybenzoic acid) is coupled as a hapten to a carrier protein to obtain the immunogen, which is used for immunization and for the subsequent cloning of suitable hybridomas.

DESCRIPTION OF THE DRAWINGS

Other objects and many attendant features of this invention will become readily appreciated as the same becomes better understood by reference to the following detailed description when considered in connection with the accompanying drawings wherein:

FIG. 1(b) shows the chemical structure formula of permethrin (1R, trans), from which the haptens according to FIG. 2 used for the production of the immunoconjugates are derived. By breaking the ester bond of permethrin, permethric acid and phenoxybenzyl alcohol are formed. For the carbodiimide coupling described below, free carboxyl groups are required; this means that phenoxybenzylic acid (BPZ) is used instead of phenoxybenzyl alcohol for the coupling with the hapten. The coupling of phenoxybenzoic acid or permethric acid is carried out in two stages. The first step of the reaction consists in the so-called "activation" of the carboxyl groups of the free acid by means of N-hydroxysuccinimide (FIG. 3) and dicyclohexylcarbodiimide (FIG. 4) (see Section 1.2, Test Conjugates, where carbodiimides link carboxyl groups to amino groups). Once the acids have been activated, it is possible for a reaction to occur between the primary amino group of N-biotinyl-1,8-diaminodioxaoctane (biotin-DADOO) and the activated carboxyl group. As a result, "biotinylated" phenoxybenzoic acid (FIG. 5) or permethric acid (FIG. 6) is obtained. Dicyclohexylcarbodiimide, which is a strong condensation agent, is hydrated to form the urea derivative.

FIG. 2 shows the haptens for the synthesis of conjugates.

FIG. 3 shows the coupling reaction of the haptens with succinimide.

FIG. 4 shows the coupling reaction of the haptens with carbodiimide.

FIG. 5 shows the biotinylation of PBZ.

FIG. 6 shows the biotinylation of permethric acid.

FIG. 7 is a schematic diagram of the hybridoma screening procedure described in Section 5. In step A, each of the microtiter plate depressions (14) is coated with 300 µL of hapten OVA conjugate (8) in 10 µg/mL in carbonate buffer (9) ("coating"). After the required washing and saturation steps, two different procedures are carried out in parallel: first, a so-called "blank" sample is processed according to steps B, C, and D, in which a direct detection of monoclonal antibodies from the culture supernatants according to Section 4, which bind to the hapten OVA conjugate, is carried out. Second, a competitive immune test is carried out (steps E, F, G) with the hapten OVA conjugate bound to the solid phase (microtiter plate depression (14)) versus free antigen in a pyrethroid solution.

For the blank sample, the pyrethroid conjugate specific monoclonal antibodies (10) are bound to the conjugate in step B and then incubated with an enzyme-marked anti-mouse antibody (11) (step C). In this case, the enzyme is a peroxidase (POD). Then an enzyme substrate (12) is added, as a result of which a color develops to indicate how much of the MAB has bonded specifically to the hapten conjugate. The results are evaluated by means of a spectrophotometric study of the microtiter plate depressions (14). For the immune test (steps E, F, G), a quantity of 100 µL of the culture supernatant according to Section 4, containing monoclonal antibodies (10), in 100 µL of PBS buffer solution, is added to each microtiter plate depression (14).

A pyrethroid mixture (13) in solution is added in excess (step E). For antibodies (10) which react with the permethric acid conjugates according to Section 1.2, the mixture (13) consists of equimolar amounts of allethrin, pyrethrin, fenfluthrin, permethrin, and cypermethrin (MIX I, FIG. 8). For monoclonal antibodies (10) which react with the phenoxybenzoic acid conjugate according to Section 1.2, the mixture (13) consists of equimolar amounts of permethrin, cypermethrin, cyfluthrin, deltamethrin, and fenvalerate (MIX II, FIG. 8). If the culture supernatant contains specific antibodies (10) against the free antigens, which are present in excess, the antibodies bond to these and not to the hapten conjugate (8) bound to the solid phase. The monoclonal antibodies (10) are then removed in a following washing step. This is followed by the addition of an enzyme-marked anti-mouse antibody (11) marked with the enzyme peroxidase (POD) and then by incubation. If all the specific antibodies (10) have found a bonding partner in the form of a free antigen (13), the anti-mouse antibody (11) cannot find a bonding partner for itself (step F). In this case, no color development occurs after the addition of the enzyme substrate (step G). If, however, some of the mouse antibodies (10) did not find a free antigen bonding partner (13) or if a non-free antigen were to bind only to the hapten conjugate (8), the subsequent addition of enzyme- marked anti-mouse antibody (11) and the addition of substrate would lead to a color development and result in an evaluatable color signal, like that already obtained for the blank sample according to steps C and D carried out in that case.

FIG. 9 is a schematic diagram of the detection of pyrethroids by means of a test kit using an ELISA immunoassay for the detection of pesticides. The antibodies are applied as a buffered solution in the form of a strip (20) to a carrier membrane (21) (step K). The ribbon-like membrane (21) has an absorbent area (22) at one end in the form of a sponge. After preparations have been completed, membrane (21) is dipped by its other end into a solution (23) containing the pyrethroids to be studied (step L). The solution also contains a defined quantity of avidin (streptavidin) enzyme conjugate. While the tip of membrane (21) is immersed in the solution (23), liquid is transported by capillary action along membrane (21) in the direction of the arrow (24). In the area of strip (20), a displacement reaction takes place on the antibody between tracer and analyte. After all of the liquid of solution (23) has been drawn up, the membrane is washed under a water faucet or with a spray bottle. Then membrane (21) is dipped into another solution (not shown) containing substrate buffer, appropriate to the nature of the enzyme conjugate, to allow the color reaction to occur between the enzyme and the substrate. An intense coloration of strip (20) (step N) indicates that no pyrethroid (analyte) was present in the sample (solution (23)), and a weaker discoloration of strip (20) (steps O, P) indicates the presence of a proportionate amount of analyte in sample (23). A measure of the quantity of analyte present in sample (23) can be derived from a comparison of the colored strip (20) with a color scale (31) (step Q), which contains six different, graduated color regions (25, 26, 27, 28, 29, 30), each having an assigned quantitative value.

DETAILED DESCRIPTION OF THE PREFERRED EMBODIMENTS

SECTION 1. SYNTHESIS OF THE CONJUGATES 1.1. Immunoconjugates: Permethric Acid Carrier or Phenoxybenzoic Acid Carrier Conjugates Immunoconjugates were synthesized as follows with the haptens cis- and trans-permethric acid and phenoxybenzoic acid.

1.1.1. Coupling Reaction for cis- and trans-Permethric Acids as the Haptens [Tijssen, supra]

Dissolve $3 \times 10^{-6}$ mole (200 mg) of bovine serum albumin (BSA) in 10 mL of distilled $H_2O$ and adjust the pH to 5.5.

Then add $10^{-4}$ mole (47 mg) of N-cyclohexyl-N'-(2-morpholinoethyl)carbo-diimide (CMC); dissolve $1.5 \times 10^{-4}$ mole (31.5 mg) of hapten (cis- or trans-permethric acid) in dimethylformamide (DMF); and add in a dropwise manner to the above solution. Check the pH and readjust if necessary.

15 minutes after the hapten has been added, add $5 \times 10^{-5}$ mole (21 mg) of CMC and stir the solution for about 12 hours at room temperature; then dialyze the solution for 48 hours against distilled $H_2O$ at 4° C., changing the water at least 4 times.

Lyophilize the hapten-BSA conjugate obtained and store it at –20° C..

1.1.2. Coupling Reaction for Phenoxybenzoic Acid as the Hapten

See Goodfriend, T. L., Levine, L. & Fasman, G. D. (1964); Antibodies to bardykinin and angiotensin; a use of Carbodiimides in immunology, Science 144, 1344–1346.

Dissolve $3 \times 10^{-6}$ mole (200 mg) of BSA in 10 mL of distilled $H_2O$ and adjust the pH to 5.5. Then add $2 \times 10^{-4}$ mole (93 mg) of N-cyclohexyl-N'-(2-morpholinoethyl) carbodiimide (CMC).

Dissolve $3 \times 10^{-4}$ mole (64 mg) of the hapten (phenoxybenzoic acid) in dimethylformamide (DMF) and add in a dropwise manner to the above solution with stirring. Check the pH and readjust if necessary.

15 minutes after the hapten has been added, add $5 \times 10^{-4}$ mole (42 mg) of CMC, and stir the solution for about 12 hours at room temperature. Then dialyze the solution for 48 hours against distilled $H_2O$ at 4° C., changing the water at least 4 times.

Lyophilize the hapten-BSA conjugate which has formed and store at –20° C.

To be able to verify whether the immunoconjugates are able to induce antibodies against the cis-/trans-permethric acid conjugates, test conjugates are required which differ with respect to the type of carrier and which also use different coupling molecules. If BSA has been used as the carrier for the immunoconjugate and CMC has been used as the coupling molecule, another albumin such as ovalbumin (OVA) should be selected for the test conjugate, and DCC and NHS should be selected as coupling molecules. In this way, it can be excluded that any positive results that may be obtained in a test for antibodies are a result of the formation of antibodies against the carrier or the bonding molecule.

1.2. Test Conjugates: Permethric Acid Carrier and Phenoxybenzoic Acid Carrier Conjugates See Märtlbauer, E. & Terplan, G. (1987): Ein enzymimmunologischer Nachweis von Chloramphenicol in Milch, Archiv f. Lebensmittelhygiene, 38, 1–7.

In separate batches, weigh $3 \times 10^{-4}$ moles of hapten (cis- and trans-permethric acid, 62 mg of each; and phenoxybenzoic acid, 64 mg). Then dissolve in pure DMF together with $3 \times 10^{-3}$ mole (620 mg) of N,N'-dicyclohexyl-carbodiimide (DCC) and $1.5 \times 10^{-3}$ mole (173 mg) of N'-hydroxysuccinimide (NHS). Incubate for 18 hours at room temperature with stirring. Dissolve $3 \times 10^{-6}$ mole (132 mg) of OVA in 7 mL of 130 mM $NaHCO_3$, and mix the above reaction mixture and the OVA solution slowly together.

Incubate for another 3 hours with stirring.

Then dialyze the solution for 48 hours against distilled $H_2O$ at 4° C., changing the water at least 4 times.

Lyophilize the resulting hapten-OVA conjugate and store at –20° C.

The hapten density (Table 1.1) per molecule of carrier or carrier protein is determined in the case of permethric acid conjugates by means of elementary chlorine analysis (Ilse Beetz, Kronach, FRG). The phenoxybenzoic acid conjugates of the CMC coupling are studied by spectrophotometry.

TABLE 1

HAPTEN DENSITIES.

| coupling method: | CMC coupling | DCC/NHS coupling |
|---|---|---|
| hapten | | |
| cis-permethric acid | 10 | 28 |
| trans-permethric acid | 12 | 25 |
| phenoxybenzoic acid | 52 | (not determinable) |

1.3. Biotin-Coupled Conjugates [Tijssen, supra]

Figure 1A:
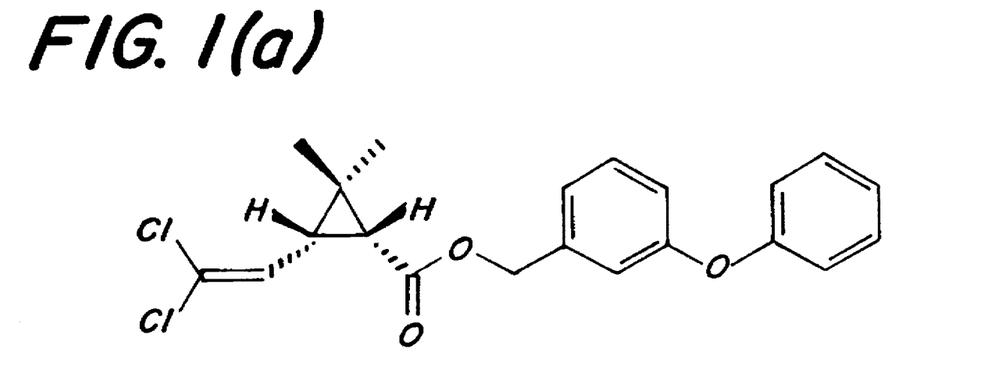
FIG. 1(a) shows the chemical structural formula of permethrin (1R, cis)
Figure 1B:
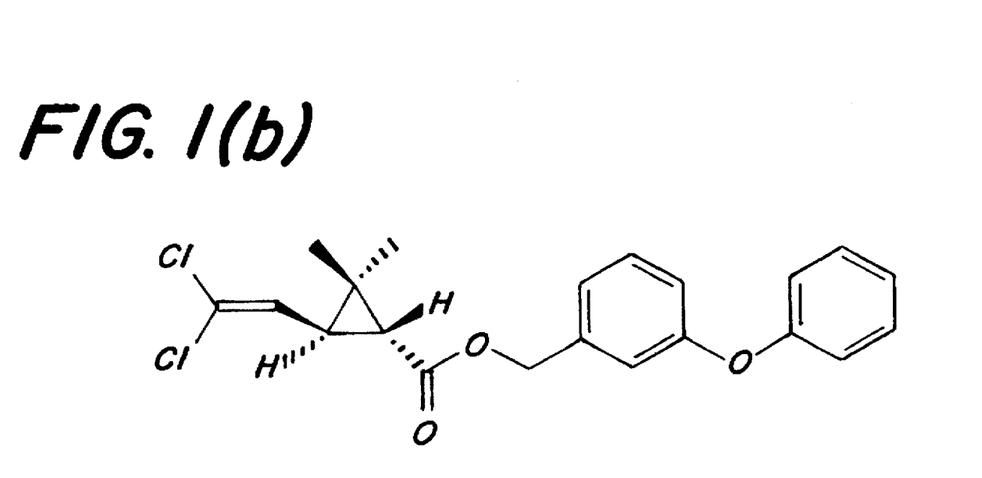
Figure 2A:
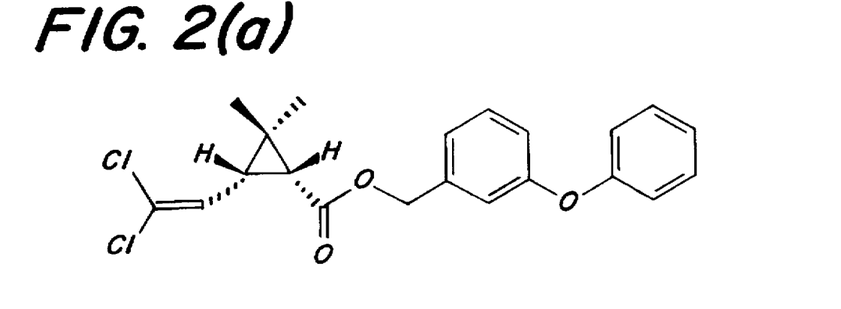
FIG. 2(a) is (1R,cis)-permethrin.
Figure 2B:
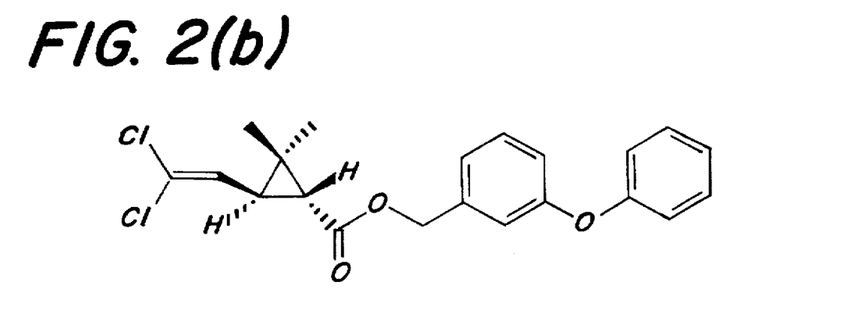
FIG. 2(b) is (1R,trans)-permethrin.
Figure 2C:
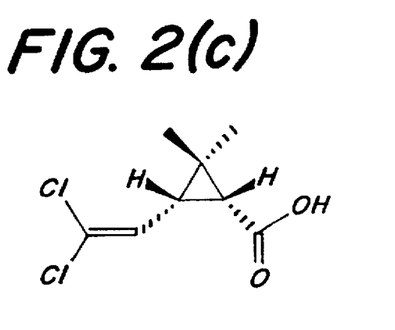
FIG. 2(c) is (1R,cis)-permethric acid.
Figure 2D:
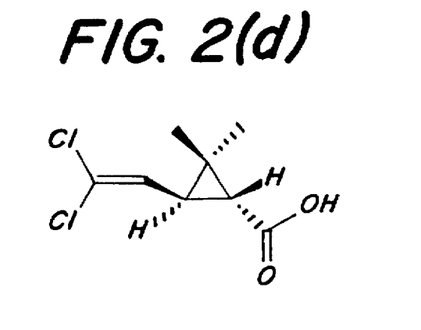
FIG. 2(d) is (1R,trans)-permethric acid.
Figure 2E:
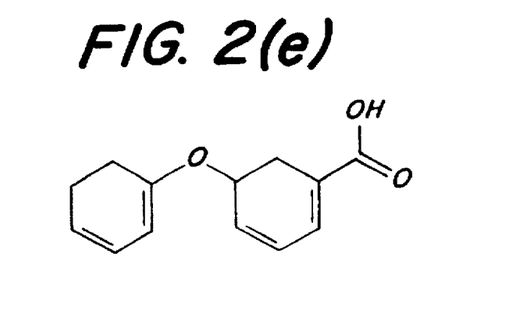
FIG. 2(e) is 3-phenoxybenzoic acid.
Figure 3A:
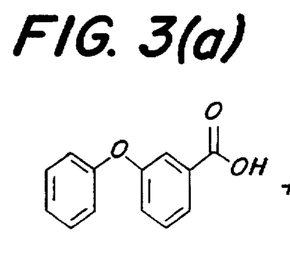
FIG. 3(a) is 3-phenoxybenzoic acid.
Figure 3B:
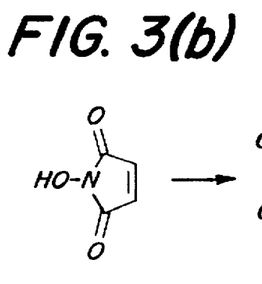
FIG. 3(b) is N-hydroxysuccinimide.
Figures 3B, 3C:
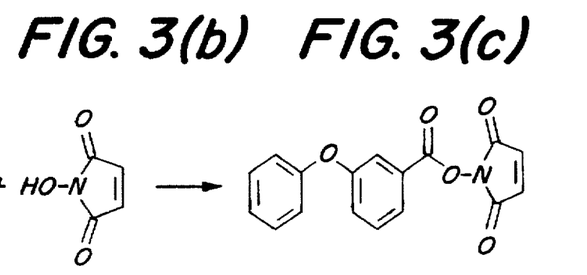
FIG. 3(c) is 3-phenoxybenzoic acid succinimide ester.
Figure 3D:
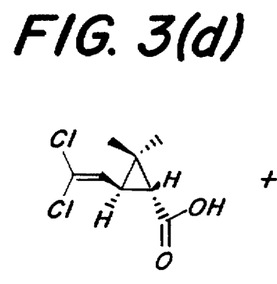
FIG. 3(d) is (1R,trans)-permethric acid.
Figure 3E:
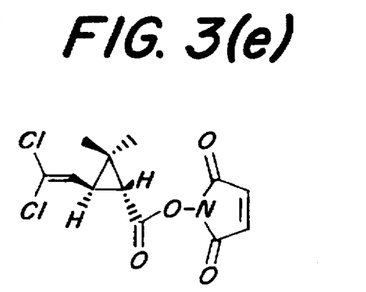
FIG. 3(e) is permethric acid succinimide ester.
Figure 4A:
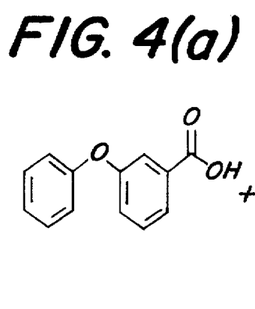
FIG. 4(a) is 3-phenoxybenzoic acid.
Figure 4B:
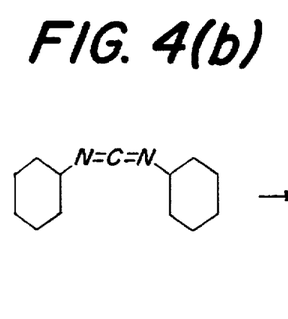
FIG. 4(b) is N,N'-dicyclohexyl-carbodiimide.
Figures 4B, 4C:
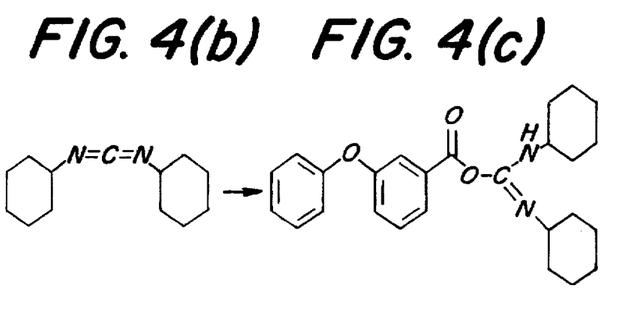
FIG. 4(c) is 3-phenoxybenzoic acid-O-acylisourea.
Figure 4D:
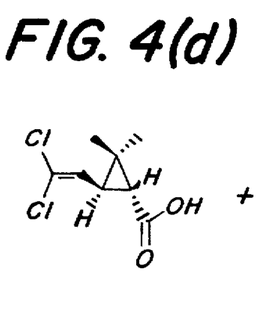
FIG. 4(d) is (1R, trans)-permethric acid.
Figure 4E:
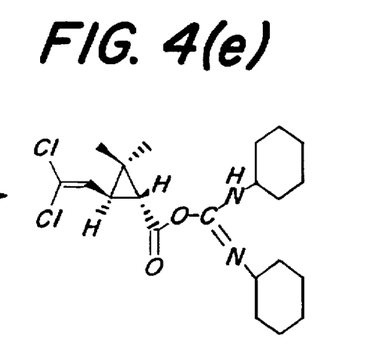
FIG. 4(e) is permethric acid-O-acylisourea.
Figures 5A, 5B, 5C, 5D:
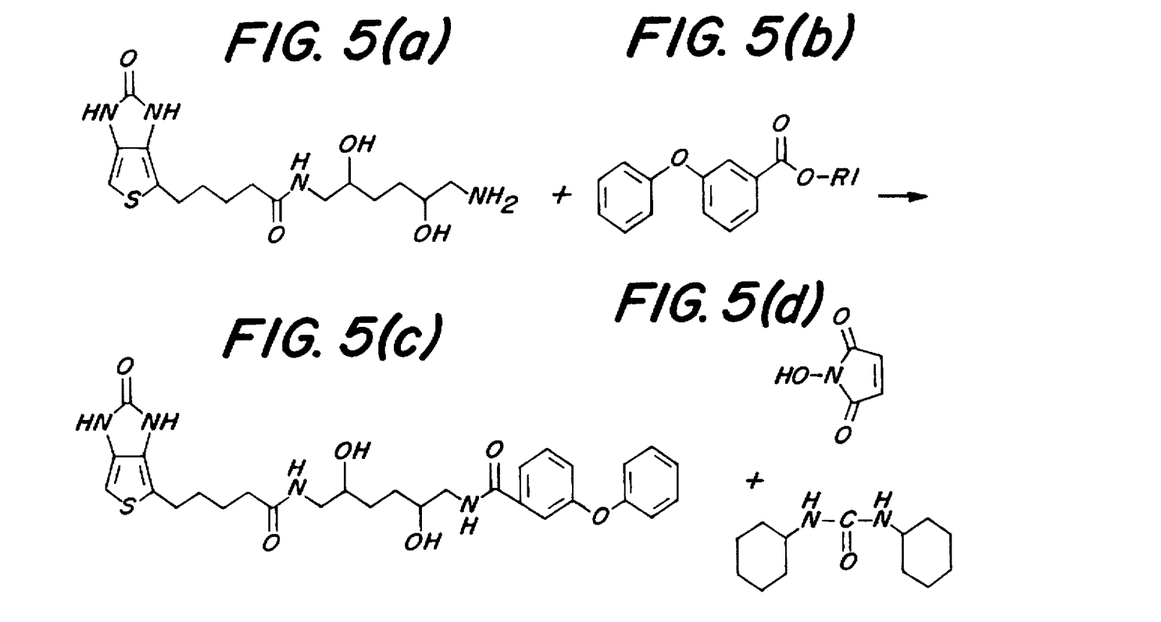
FIG. 5(a) is N-biotinyl-1,8-diaminodioxaoctane.
FIG. 5(b) is activated phenoxybenzoic acid.
FIG. 5(c) is phenoxybenzoic acid-(C8)-biotin.
FIG. 5(d) is N,N'-dicyclohexylisourea.
Figure 6A:
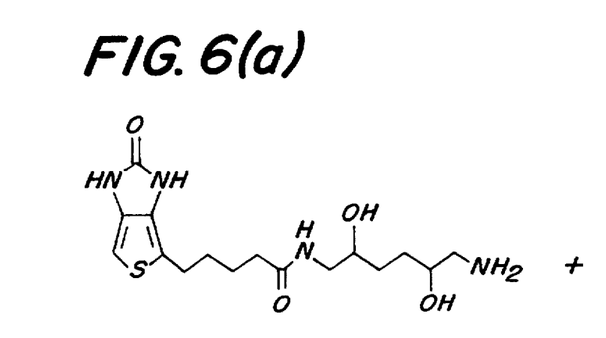
FIG. 6(a) is N-biotinyl-1,8-diaminodioxaoctane.
Figure 6B:
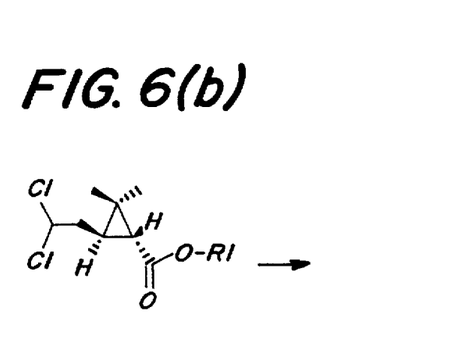
FIG. 6(b) is activated (1R,trans)-permethric acid.
Figures 6C, 6D, 6E:
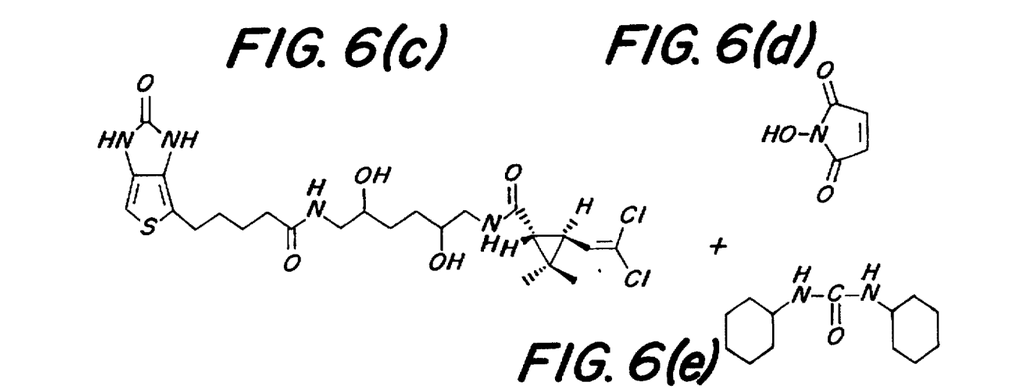
FIG. 6(c) is N-hydroxysuccinimide.
FIG. 6(d) is permethric acid-(C8)-biotin.
FIG. 6(e) is N,N'-dicyclohexylisourea.
Figure 7A:
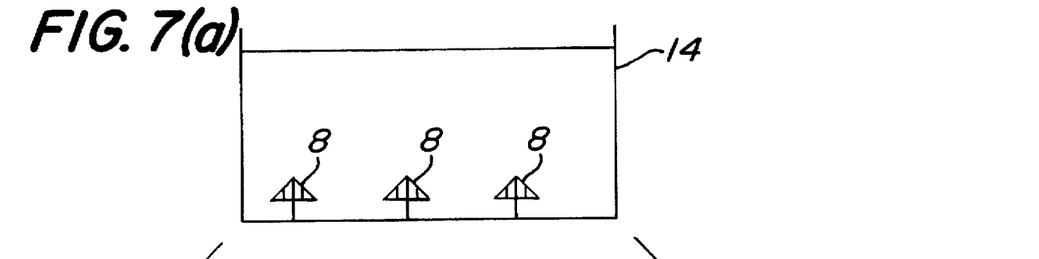
Figure 7B:
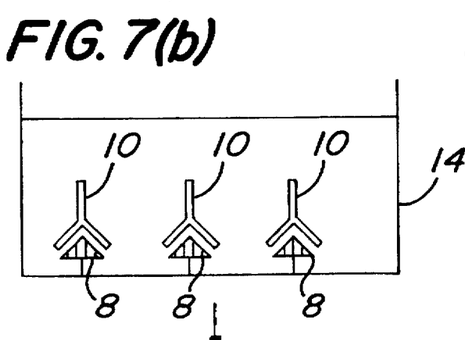
Figure 7C:
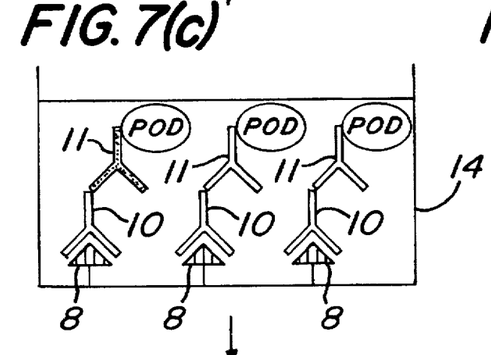
Figure 7D:
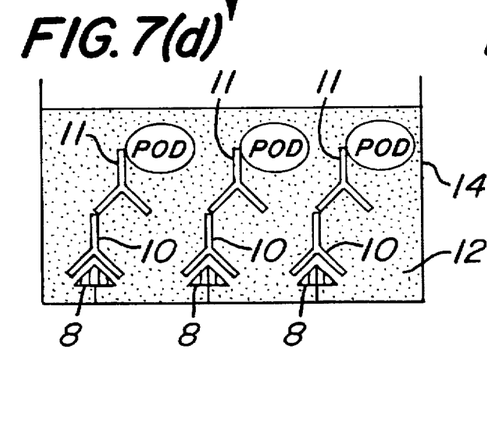
Figure 7E:
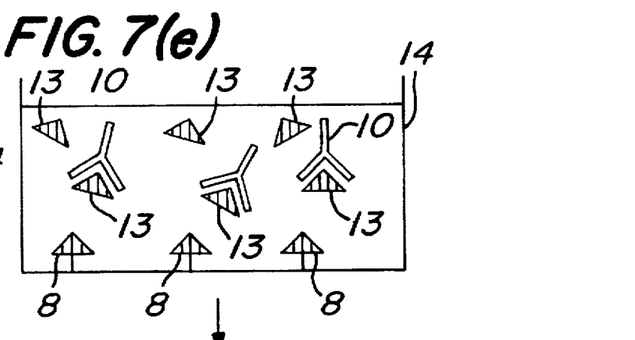
Figure 7F:
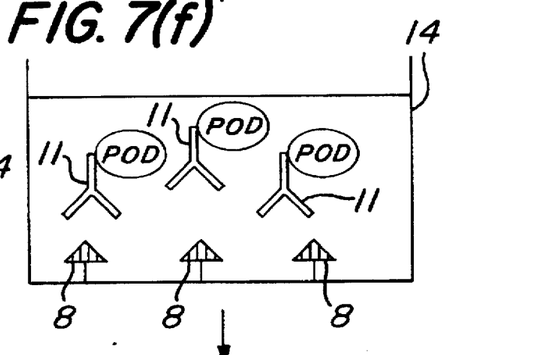
Figure 7G:
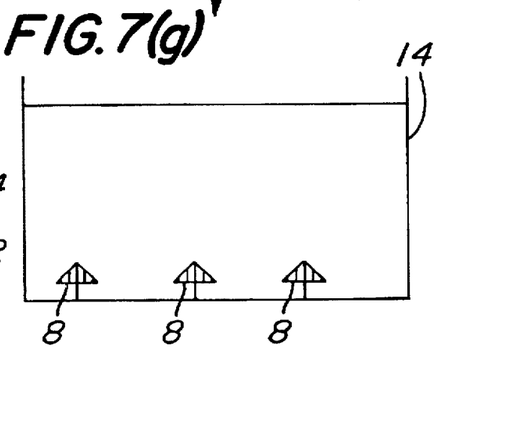

It was found that enzyme-marked tracers suitable for use in immunoassays can be obtained by the biotinylation of the haptens cis-/trans-permethric acid and phenoxybenzoic acid: The derivatized hapten can be linked to one or more markers or indicators by way of the known (strept)avidin-biotin marking system. For example, the hapten enzyme conjugate can be produced by coupling a reactive biotin ester to the hapten by way of a spacer. After activation, i.e., esterification, of the hapten with NHS or DCC (FIGS. 3 and 4), the hapten is biotinylated by reacting it with, for example, N-biotinyl-1,8-di-amino-3,6-dioxaoctane (biotin-DADOO) (FIGS. 5 and 6).

SECTION 2. IMMUNIZATION

The immunization of female, 4-6-week-old BALB/c mice is carried out in accordance with the immunization plan shown in Table 2. The conjugate is injected intraperitoneally. After the first administration, Freund's complete adjuvant is replaced by the incomplete adjuvant.

TABLE 2

IMMUNIZATION PROTOCOL.

| Week | Immunogen Administration | Quantity of Immunogen | Freund's Adjuvant | Blood Sample |
|---|---|---|---|---|
| 0 | 1st | 50 μg | complete | |
| 4 | 2nd | 50 μg | incomplete | |
| 8 | 3rd | 50 μg | incomplete | |
| 10 | — | — | — | 1st test blood |
| 12 | 4th | 50 μg | incomplete | |
| 14 | — | — | — | 2nd test blood |

On days 3, 2, and 1 before the removal of the spleen, additional intraperitoneal booster injections are given, each consisting of 400 μg of immunoconjugate in 200 μL of saline solution (0.9%). The mice are then killed, and the spleens taken out, cut into portions and cryopreserved; isolated spleen cells are fused with myeloma cells PAI-B3Ag81. Stocker, J. W. et al. (1982): Generation of 2 new mouse myeloma cell lines "PAI" and "PAI-O" for hybridoma production. Hoffmann-La Roche Research Disclosure, 21713, 155–157.

The fusion of spleen cells with myeloma cells to form hybridomas is described in the following protocol.

SECTION 3. FUSION PROTOCOL

Myeloma cell line PAI-B3Ag81, a myeloma cell line which does not secrete any antibodies itself and which is described in Stocker et al., was cultivated in accordance with known cell culture methods as described by way of example in Lindl, T. and J. Bauer (Editors): Zell - und Gewebekultur, Einführung in die Grundlagen sowie ausgewählte Methoden und Anwendungen, (Cell and Tissue Culture, Introduction to the Principles and Selected Methods and Applications) Gustau Fischer Verlag, Stuttgart, Federal Republic of Germany (1989); and in Peters, J. H. & Baumgarten, H., Hrsg. (1990): Monoklonale Antikörper: Herstellung und Charakterisierung, Springer-Verlag, Berlin, BRD.

The removal of the spleen from the BALB/c mice immunized in accordance with Section 2, the recovery of the spleen cell suspension for cell fusion, and the polyethylene glycol-mediated fusion of the spleen cells with the myeloma cells were also carried out on the basis of or in accordance with previously described methods known to those skilled in the art, see Harlow & Lane, supra. After the cultivation of the myeloma cell lines, the desired hybrid cells were selected.

SECTION 4. CULTIVATION OF THE HYBRID CELLS

The cultivation and selection of the desired hybridoma cells by means of HAT and HT selection were carried out according to the method of Peters & Baumgarten, supra. On the 1st day after cell fusion, fresh HAT medium was added to the cell cultures, three to five days after cell fusion, the fused cells were checked under the microscope. At the same time, the medium was changed for the first time. After three more days, the culture medium was changed again. On the seventh and tenth days after cell fusion, the depressions in the cell culture vessels were searched for hybrids, and the medium was renewed two to three times per week. After about two weeks, the HAT medium was replaced by HT medium. The supernatant of washed hybrid cultures was decanted and tested for the presence of antibodies (see Section 5). Monoclonal antibody-secreting cell colonies were then cloned by the limited dilution method known to those skilled in the art (clones).

The next step was to determine whether or not the hybridoma clones thus obtained produced the desired antibodies.

SECTION 5. HYBRIDOMA SCREENING

The screening conjugates described in Section 1.2 were used for this purpose. In addition, "Maxisorp" (from the Nunc Corporation) microtiter plates were used. The immunoscreening method, i.e., an indirect, competitive immunoassay with free antibodies, is shown in the form of a schematic diagram in FIG. 7. First, each of the microtiter plate depressions was coated with 300 µL of hapten OVA conjugate (10 µg/mL in carbonate buffer) (coating). This was carded out over the course of 15–18 hours at 4° C. Then the depressions were washed 3 times with, for example, PBS Tween 20 buffer. To block the unoccupied bonding sites on the microtiter plate, about 300 µL of 0.1% OVA solution was added to each depression. This batch was incubated for 1–2 hours and then washed again as described. To verify the results, two separate screening processes were used (FIG. 7):

5.1. DIRECT DETECTION

Monoclonal antibodies from the culture supernatants according to Section 4 which bond to the hapten-OVA conjugate (Section 1.2) are detected directly.

5.2. COMPETITIVE IMMUNOASSAY

In this immunoassay, the hapten-OVA conjugates bound in the solid phase (Section 1.2) compete with the free antigen in the form of a solution of a mixture of pyrethroids. For the direct detection (Section 5.1), 100 µL of PBS buffer and 100 µL of cell culture supernatant (Section 4) per depression are incubated for one hour at room temperature under gentle agitation. Then a washing step is carried out with PBS Tween 20 buffer. This is followed by incubation with the peroxidase-(POD)-conjugated anti-mouse antibodies known to those skilled in the art. After the addition of enzyme substrate, the color is developed. The reaction is stopped after 30 minutes with 2N $H_2SO_4$ and evaluated by spectrophotometry. The positive hybridoma cells, which secrete a specific antibody, give a strong color signal.

A positive signal at the end of the direct detection process gives the certainty that the antibodies from the culture supernatants according to Section 4 are in fact able to react to the test conjugate containing a structural component of the pyrethroids/pyrethrum. The attempt to produce monoclonal antibodies which react to a pyrethroid-specific group or structural component has therefore been successful. Direct detection, however, makes it possible to state only whether antibodies have been formed or not. It is impossible to differentiate among the antibodies with respect to their affinity for a specific pyrethroid or group of pyrethroids. For this purpose, the competitive immunoassay according to Section 5.2 is used.

Figure 8:
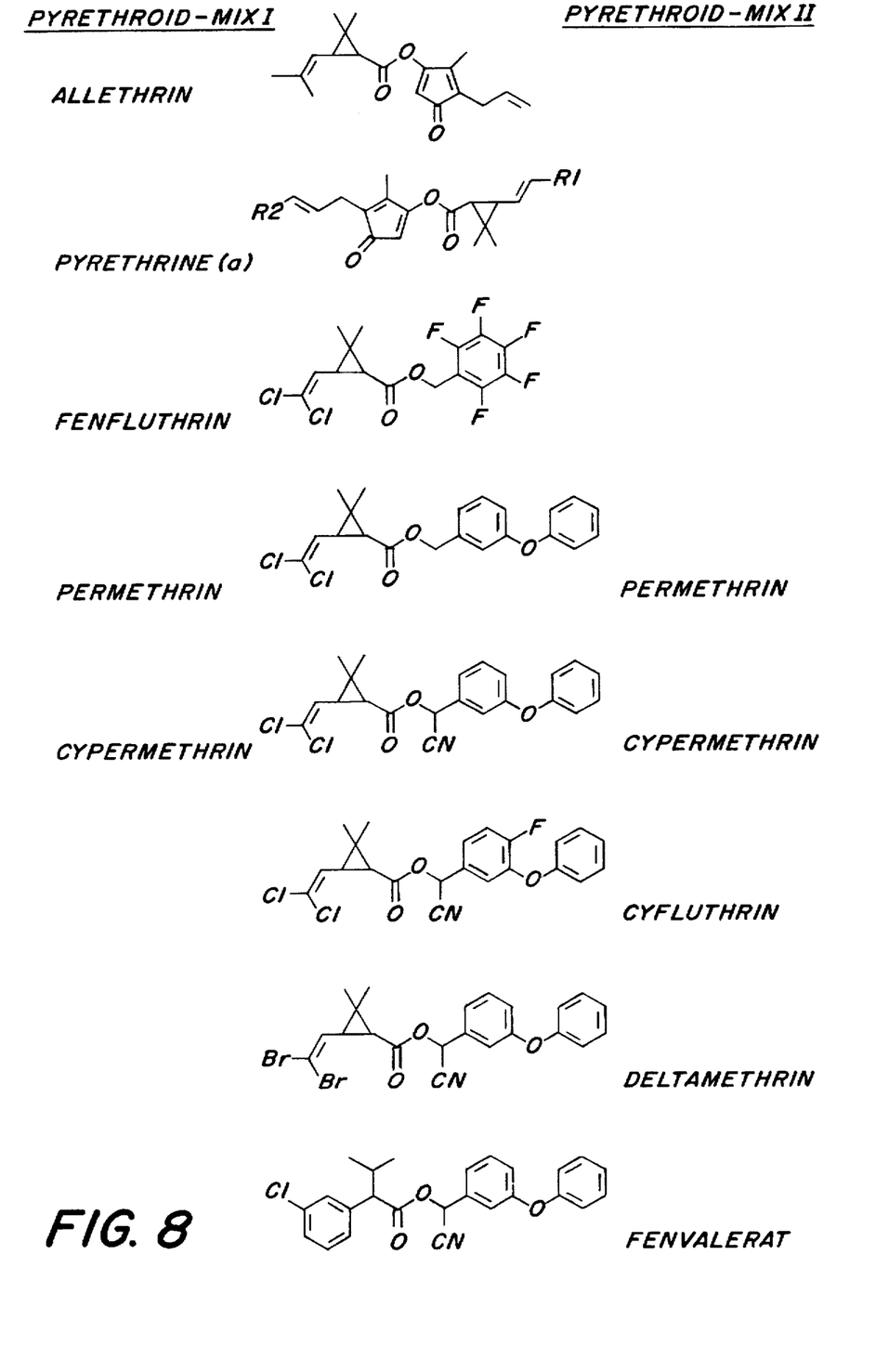
FIG. 8 is a summary of the excess solutions MIX I/MIX II for the screening process shown in FIG. 7.
Figures 9K, 9L:
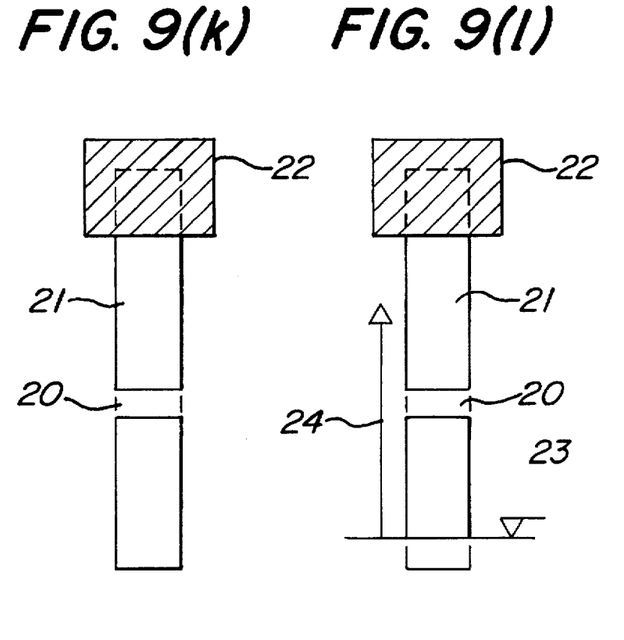
Figure 9M:
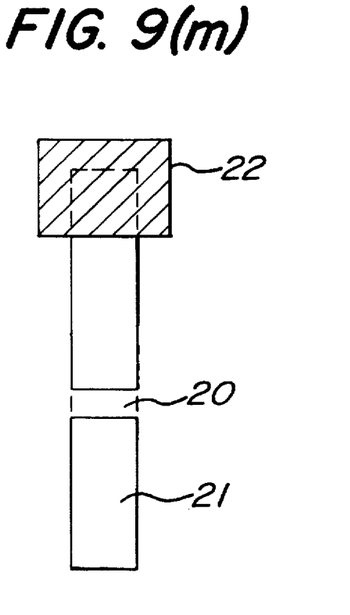
Figures 9N, 9O:
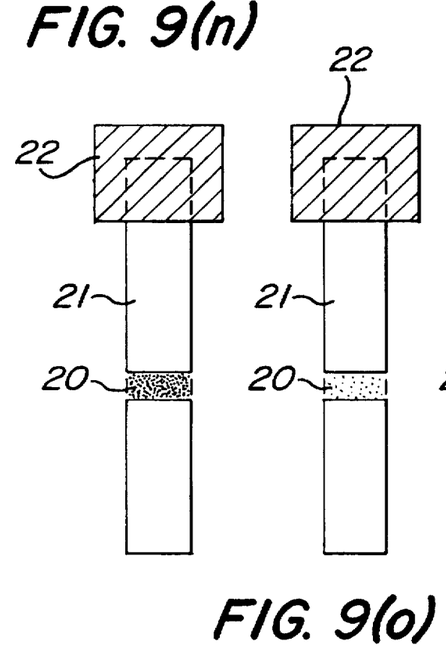
Figures 9P, 9Q:
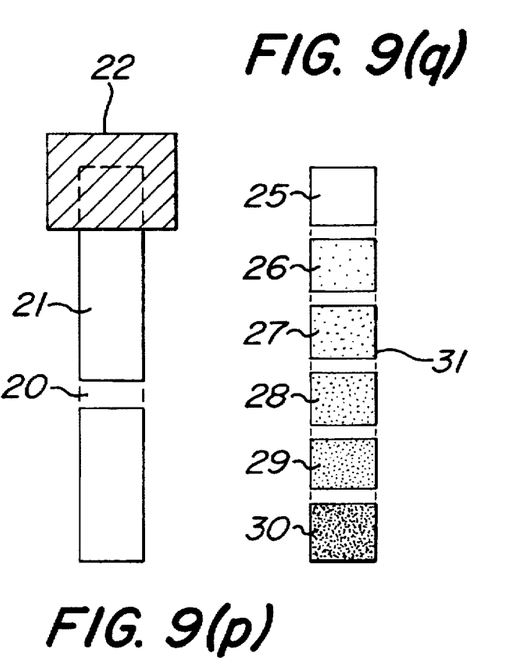

The analyte in this case consists of a solution of a mixture of pyrethroid substances in excess. For the antibodies which react with permethric acid conjugate (Section 1.2), the mixture can consist of equimolar amounts of, for example, allethrin, pyrethrum, fenfluthrin, permethrin, cypermethrin (FIG. 8, MIX I); and, for the antibodies which bind specifically to the phenoxybenzoic acid conjugate (Section 1.2), the pyrethroid mixture can consist of equimolar amounts of, for example, permethrin, cypermethrin, cyfluthrin, deltamethrin, and fenvalerate (FIG. 8, MIX II).

For this purpose, 100 µL of analyte solution (10 mg/L of pyrethroid substance in mixture MIX I/II in PBS buffed and 100 µL of culture supernatant (Section 4) per depression in the microtiter plate are incubated for 1 hour at room temperature.

If the cell culture supernatant contains specific antibodies with high affinity for at least one substance in the mixture in question (MIX I/II), these bind to the free hapten present in excess (pyrethrins/pyrethroids) and not to the hapten conjugate bound in the solid phase. The monoclonal antibodies bound to the hapten are then removed in the following washing step. This is followed by the incubation, known to those skilled in the art, with peroxidase-(POD)-conjugated anti-mouse antibodies and by subsequent addition of enzyme substrate and color development. After a predetermined incubation time, the microtiter plates are evaluated by spectrophotometry. Positive hybridoma cells which secrete an antibody selective for the pyrethroids in MIX I/II give a weaker color signal or no signal at all. Hybridoma cells which secrete antibodies which bind non-specifically to the hapten conjugate cannot be displaced by the excess pyrethroid and give a corresponding color signal. If no antibodies are present in the culture supernatant, there is no color reaction in either of the two cases.

The following compositions were selected for the EIA substrate and the EIA chromogen:
substrate (pH 5.5):
1.25 g/L of $Na_2HPO_4.2H_2O$ (7 mM);
18.20 g/L of $NaH_2PO_4.H_2O$ (132 mM); and
282 mg/L of urea hydrogen peroxide (Aldrich Cat. No. 28,913-2).

chromogen (pH 2.6):

Dissolve 288 mg of 3,3',5,5'-tetramethylbenzidine (Sigma T-2885) in 100 mL of DMSO. Fill to the one liter mark with distilled $H_2O$, then add 0.5 mL of phosphoric acid and 12 mg of penicillin G.

A utility mixture consists of 1 part of chromogen and 2 parts of substrate. 200 µL is added to each depression in the microtiter plate.

In the case of a double-positive signal, i.e., both from the direct detection (Section 5.1) and from the competitive immunoassay (Section 5.2), it is certain that the antibodies contained in the culture supernatant (Section 4) respond selectively to at least one substance in the pyrethroid mixture MIX I or MIX II. Further information on the specific selectivity/affinity for individual pyrethroids is obtained by corresponding studies of the cross-reactivity (see Section 7).

The procedural steps described so far for the production and detection of monoclonal antibodies sensitive to pyrethroids which, as a functional structural component, have a cyclopropanoic acid derivative and/or phenoxybenzoic acid, can be summarized as follows:

1. The synthesis of immunoconjugates consisting of cis-/trans-permethric acid or phenoxybenzoic acid bound to BSA by way of CMC; the synthesis of test conjugates consisting of cis-/trans-permethric acid or phenoxybenzoic acid bound to OVA by way of DCC/NHS.
2. The immunization of BALB/c mice.
3. The fusion of spleen cells with myeloma cells (hybridomas).
4. The cultivation of the hybridoma cells and their separation from the other cells by introducing them into a specific medium in which only hybridomas can survive.
5. The isolation of the hybridomas reacting specifically to pyrethroids from the other hybridoma cells over the course of several series of screening tests.

The hybridoma cells obtained after the fifth step are propagated in cell cultures, and the monoclonal antibodies are therefore produced continuously.

The monoclonal antibodies can now be used to detect pesticides and insecticides containing pyrethroids which have a functional group consisting of permethric acid and/or phenoxybenzoic acid:

SECTION 6. PESTICIDE/INSECTICIDE DETECTION

Pyrethrum, pyrethroids, their derivatives, and/or their metabolites are detected with the help of the hapten screening conjugates and biotin tracers described in Section 1 and by the use of the competitive immunoassay (ELISA) described in Section 5.

First, the test procedure is described in general on the basis of a competitive test (ELISA=enzyme-linked immunosorbent assay).

In the competitive test, a competition takes place for antibody binding sites between an unmarked analyte of unknown quantity (here: pyrethroid) and a tracer (marked hapten) of known quantity. The antibody is immobilized on a solid phase. Depending on the amount of tracer and unmarked analyte in the sample, the antibody binding sites are occupied to a greater or lesser extent by tracer and analyte. The tracer is detected by an enzymatic color reaction, which means that the detection signal on the solid phase is inversely proportional to the amount of analyte detected.

In the direct-competitive test for low-molecular substances such as pyrethroids, a competition for a constant number of antibody binding sites takes place between an unmarked analyte of unknown quantity (here: pyrethroid) and a tracer (marked hapten) of known quantity. The antibody is immobilized on a solid phase. Depending on the amount of unmarked analyte in the sample, the antibody binding sites are occupied to a greater or lesser extent by tracer or analyte. The tracer is detected by a color reaction, which means that the detection signal on the solid phase is inversely proportional to the amount of analyte detected. The color development is measured by spectrophotometry at a defined wavelength. The wavelength to be used depends on the substrate and the chromogen. In the case of the composition used here (see Section 5.2), the wavelength is 450 nm. Several samples to be studied are diluted to different degrees. The dilutions of the individual samples are selected so that absorption values in a range of, for example, 0.7–1.0 are obtained without the addition of an analyte (i.e., without inhibitor=$B_o$). For verification (e.g., without antibodies or without enzyme), absorption values of less 0.005 are obtained. Three determinations are made of the samples. For the determination of the amount of pyrethrins/pyrethroids (analyte) in a sample, a calibration curve is first set up where $B/B_o \times 100$ is plotted versus the concentration of inhibitor ($B/B_o$=enzyme tracer bonding in the presence of an analyte (B) of known quantity in relationship to the enzyme tracer bonding in the absence of an analyte ($B_o$)). In the indirect competitive test selected here, the central test point (50% $B/B_o$) gives the concentration of the analyte at which the binding of the antibody to the solid phase experiences 50% inhibition ($B/B_o$ value). When $B/B_o$ is plotted on the Y axis versus the logarithm of the analyte concentration, an S-shaped curve is obtained. The 50% $B/B_o$ value is calculated on the basis of the transformation of the values according to the logit-log method or the four-parameter method Rodbard, D. (1978): Data processing for radioimmunoassay: An overview In Clinical Immunoassay: Cellular Basis and Applications in Disease. (Natelson, Pesce & Dietz., Hrsg.), Am. Assoc. for Clin. Chem., Washington D.C., 477–494; and Rodgers, R. P. C. (1984): Data analysis and quality control of assays: a practical primer, in: Practical Immunoassay, the state of the art (Butt, W. R. Hrsg.), Dekker-Verlag, New York, 253–308.

So that a competitive immunoassay (ELISA) can be carried out conveniently, a test kit can be assembled such as that described in German Patent Application File No. P 4,229,591.2. FIG. 9 shows a schematic diagram of the procedure for an immunoassay carried out by means of a test kit of this type. The test described here by way of example is a displacement test.

This form of the immunoassay is based on the displacement of an immobilized enzyme-marked hapten (tracer) in the solid phase by an unmarked antigen or hapten in the free phase (solution). The displacement is made possible by the difference between the affinity constants of the enzyme-marked and the free antigen. In the measurement of the enzyme activity, the detection signal is again inversely proportional to the amount of analyte in the sample, as it was in the competitive assay on the solid phase described further above.

The antibodies are applied as a buffered solution (a suitable concentration being 1 mg/mL) in the form of strips to the membrane being used. Suitable for this purpose is, for example, the Linomat IV (Camag). This results typically in 0.5 µg of protein per membrane strip. Then the membrane is dried in air at room temperature (about 22°–25° C.). The binding sites on the test strip which are not yet occupied by the antibodies and are still free are blocked by incubation of the membrane in saturation reagents.

Known saturation reagents include, for example, 3–5% (v/v) horse serum (HSA) in phosphate-buffered solution (PBS) and 0.25% (w/v) casein (Merck)+0.1% (v/v) Triton X-100 (Rohm & Haas) in PBS. After the saturation step, there follows a washing step with 0.1% (v/v) Tween 20 (Merck) in PBS solution to remove excess saturation reagent. This is followed by incubation with the tracer produced according to Section 1.3, which is added in excess with respect to the immobilized antibodies to saturate all possible antibody binding sites. Then, as described above, another washing step in Tween/PBS solution is carried out. After that, the test strip is dried, or it can be used immediately for a pyrethroid or pyrethrin MIDA test as described in Patent Application No. P 4,229,591.2 (FIG. 9). For this purpose, the prepared test strip is placed in a holder. Test strip and holder are then placed, for example, in the cover of the test unit, which is designed as a glass container. Then the solution with the analyte (the sample containing the insecticide) is transferred to the sample container. In the sample container there is also a defined amount of, for example, an avidin enzyme conjugate, preferably a streptavidin enzyme conjugate. The test strip is now placed in the sample container in such a way that the lower edge of the strip dips into the sample. As a result of the capillary transport of the liquid which now occurs, the substances in the sample vessel are carried over or through the membranes. Thus the displacement reaction between tracer and analyte occurs at the intended location. After a given time or after all of the sample liquid has been absorbed, the membrane strip is removed from the sample container and rinsed off under a water faucet, for example, or by the use of a laboratory spray bottle. Then the test strip is transferred to a second container (substrate container), which contains the substrate buffer in aqueous solution or the corresponding substances in lyophilized form. In the case of lyophilized substances, these are first rehydrated with a prescribed amount of, for example, water. The substrate buffers are always selected to suit the corresponding enzyme conjugate. For example, here is the composition for alkaline phosphatase:

substrate buffer:

0.1 mole/L $NaHCO_3$, 0.001 mole/L $MgCl_2$, 0.70 mmole/L NBT, and 0.30 mmole/L BCIP.

BCIP=5-bromo-4-chloro-3-indolyl phosphate disodium salt (stock solution in dimethyl formamide=DMF);

NBT=2,2'-di-p-nitrophenyl-5,5'-diphenyl-3,3'-(3,3'-dimethoxy-4,4,'-diphenyl)ditetrazolium chloride.

After a predetermined reaction time (e.g., 1–2 minutes), the reaction is stopped by rinsing the test strip with water, and the coloration obtained is compared with a color scale for evaluation. An intense color shows that no pesticide is present in the sample or that the amount in this test is below the detection threshold and therefore no detectable displacement of tracer has occurred. No color development shows that the tracer has been displaced completely and that therefore there is a high content of pesticide in the sample solution. Possible intermediate stages in the coloration are a measure of the analyte concentration in the sample. In this example, the color intensity is inversely proportional to the measured analyte concentration. Additional embodiments or types of MIDA tests and test kits which can be assembled for the detection of pyrethroids or pyrethrins and their derivatives and a description concerning the use of such kits as multi-analyte units are described by way of example in German Patent Application File No. 4,229,591.2.

SECTION 7. CROSS-REACTIVITY

The quality and specificity of the monoclonal antibodies obtained are discussed in the following in the form of a protocol of the results of completed studies.

Only a few days after the fusion of the myeloma cells with the spleen cells of the mice which had been immunized separately with the hapten immunoconjugates described in Section 1.1 (cis- and trans-permethric acid and phenoxybenzoic acid), proliferating cell colonies could be detected in the depressions of the culture containers. A hybridoma screening was carried out as described in Section 5. For example, after the immunization with trans-permethric acid conjugate and the fusion of the spleen cells with the myeloma cells, 15 propagation plates, each with 96 depressions, were studied. Thirty cell colonies were found to be producing monoclonal antibodies, and ultimately 4 cell colonies were found by the test method described to be synthesizing monoclonal antibodies with the desired properties. These antibodies belonged to subclass IgGl. On the basis of their cross reactivities as determined in the ELISA test, the monoclonal antibodies obtained in this way could be divided into 2 groups. In the first group (represented by the monoclonal antibodies of myeloma cell line 3/B4-1/F8), the cross reactivity was found to be limited to natural pyrethrins and synthetic pyrethroids. In addition, the known dot test (dot immuno-binding assay) revealed different selectivities for the two isomeric permethric acid haptens. The isolated monoclonal antibodies had a much higher affinity for the trans-PMS hapten immunoconjugate than for the cis-PMS hapten conjugate (PMS=permethric acid). The second group (represented by the monoclonal antibodies of myeloma cell line 1/E2-5/B5) is characterized by a selectivity for allethrin, bioallethrin, and phenothrin. The cross-reactivities occurring here with respect to other pyrethroids are negligible. The lower detection limits for pyrethrins/pyrethroids are in the range of 10–80 ng/mL of buffer. The corresponding 50% $B/B_o$ values are between 40 and 400 ng/mL.

In neither group was there any cross reactivity with the phenoxybenzoic acid hapten conjugate (PBZ) or with pyrethroids which contain PBZ as the only pesticide-characteristic structural component. It was surprising to discover that the isolated monoclonal antibodies showed little or no cross-reactivity with respect to free cis- or trans-permethric acid.

In the past, it was impossible to isolate any monoclonal antibodies with a similar type of cross reactivity or a similar degree of hapten stereoisomer specificity when cis-permethric acid immunoconjugates or PBZ immunoconjugates were used.

The observed cross reactivities are summarized in the following table:

TABLE 3

| (a) Inhibitor, (analyte) | (b) hybridoma clone MAB 3/B4-1/F8 % cross reactivity | (c) hybridoma clone MAB 1/E2-5/B5 % cross reactivity |
|---|---|---|
| allethrin | 45 | 100 |
| bioallethrin | 100 | 104 |
| cyfluthrin | n.b. | 6, 7 |
| cypermethrin | n.b. | 6, 4 |
| deltamethrin | n.b. | n.b. |
| fenfluthrin | 2 | 13 |
| fenvalerat | n.b. | n.b. |
| pyrethrine | 26 | 1 |

TABLE 3-continued

| (a) Inhibitor, (analyte) | (b) hybridoma clone MAB 3/B4-1/F8 % cross reactivity | (c) hybridoma clone MAB 1/E2-5/B5 % cross reactivity |
|---|---|---|
| permethrin | n.b. | 5, 8 |
| phenothrin | n.b. | 86 |
| cis-PMS | n.b. | n.b. |
| trans-PMS | n.b. | >1 |
| PBZ | n.b. | n.b. |
| CTS | n.b. | n.b. |

The following abbreviations/definitions are used in the table:
n.b. = not determinable
PMS = permethric acid
PBZ = phenoxybenzoic acid
CTS = chrysanthemum acid $$\text{Cross reactivity }(\%) = \frac{50\% \text{ B/B}_o \text{ (µg/L) of the analyte}}{50\% \text{ B/B}_o \text{ (µg/L) of the cross-reacting substance}} \times 100$$

Concerning the nomenclature of the monoclonal antibodies such as 3/B4-1/F8:

3=plate no. of the first propagation;

B4=coordinates of the plate cavity of the first propagation;

1=plate no. during cloning; and

F8=coordinates of the plate cavity during cloning.

The hybridoma cell lines produced and used within the scope of the present invention are on deposit at the "Deutsche Sammlung yon Mikroorganismen GmbH". (German Collection of Microorganisms Co. Ltd.) in Braunschweig (Federal Republic of Germany), which is recognized as an international depository, in correspondence with the applicable requirements of the Budapest Treaty on International Recognition of the Deposition of Cell Cultures for the Purpose of Patenting.

A declaration on the viability ("viability certification") of the deposited samples (receipt no.) has been prepared by the depository.

| Cell Line | Deposition Date | Receipt No. | Certification Date |
|---|---|---|---|
| 3/B4-1/F8 | July 1, 1993 | DSM ACC 2135 | July 12, 1993 |
| 1/E2-5/B5 | July 1, 1993 | DSM ACC 2136 | July 12, 1993 |

The media and buffers used within the scope of the test series, syntheses, and tests are listed in the following table:

TABLE OF MEDIA AND BUFFERS (A) standard medium (RPMI 1640)
   500 mL of RPMI with HEPES (Tecnomara)
   55 mL of FCS (Fetal Calf Serum) (Tecnomara)
   5.5 mL of 200 mM glutamine
   5.5 mL of $10^{-3}$M mercaptoethanol solution
(B) HAT medium, stock solution
   $10^{-2}$M hypoxanthine (Merck)
   $10^{-5}$M aminopterin (Serva)
   $10^{-3}$M thymidine (Sigma)
Add 5.5 mL of each of these stock solutions to 570 mL of standard medium.
(C) HT medium
   Add 5.5 mL of the stock solution of hypoxanthine and 5.5 mL of the stock solution of thymidine to 570 mL of the standard medium.
(D) freezing medium
   70 mL of RPMI medium without HEPES
   20 mL of FCS
   12 mL of DMSO
   1 mL of $10^{-1}$M mercaptoethanol
(E) PBS buffer (pH 7.6)
   150 mM NaCl
   2 mM $Na_2HPO_4$
   8 mM $NaH_2PO_4$
(F) PBS Tween 20 (0.05%)
   0.5 mL of Tween 20 (Serva)+1.000 mL of PBS buffer (Tween 20=polyoxyethylene sorbitan monolaurate)
(G) carbonate buffer (pH 9.6)
   16 mM $Na_2CO_3$
   34 mM $NaHCO_3$ Without further elaboration the foregoing will so fully illustrate our invention that others may, by applying current or future knowledge, adapt the same for use under various conditions of service.

BIBLIOGRAPHY

The following specialized literature and patent publications are cited with respect to the state of the art:

SPECIALIZED LITERATURE (1) Goodfriend, T. L., Levine, L. & Fasman, G. D. (1964); Antibodies to bardykinin and Angiotensin; a use of Carbodiimides in immunology. Science 144, 1344–1346.

(2) Harlow, E. & Lane, D., Hrsg., (1988) Antibodies, a laboratory manual, Cold Spring Harbor Lab., Cold Spring Harbor, USA.

(3) Burrin, J. & Newman, D. (1992): "Production and assessment of antibodies"; In: Principles and practice of immunoassay, (Price, C. P. & Newman, D. Hrsg.), Stockton press, New York, USA.

(4) Campbell, A. M., (1991): "Monoclonal antibody and immunsensor technology"; Laboratory techniques in biochemistry and molecular biology, 23, (van der Vliet, P. C., Hrsg.) Elsevier science publishers B.V., Amsterdam, NL.

(5) Leahey, J. P. Hrsg., (1985): The Pyrethroid Insecticides, Taylor & Francis Ltd. London UK.

(6) Unkl, T. & Bauer, J., Hrsg., (1989): Zell - and Gewebekultur, Einführung in die Grundlagen sowie ausgewählte Methoden und Anwendungen, Gustav Fischer Verlag, Stuttgart, BRD.

(7) Märtlbauer, E. & Terplan, G. (1987): Ein enzymimmunologischer Nachweis von Chloramphenicol in Milch. Archiv f. Lebensmittelhygiene, 38, 1–7.

(8) Naumann, K., (1981): Chemie der synthetischen Pyrethroid-Insektizide, Band 7: Chemie der Pflanzenschutz - und Schädlingsbekämpfungsmittel, (Wegler, R., Hrsg.), Springer-Verlag, Berlin, Heidelberg, BRD.

(9) Peters, J. H. & Baumgarten, H., Hrsg. (1990): Monoklonale Antikörper: Herstellung und Charakterisierung, Springer-Verlag, Berlin, BRD.

(10) Rodbard, D. (1978): Data processing for radioimmunoassay: an overview., in: Clinical Immunoassay: cellular basis and applications in disease. (Natelson, Pesce & Dietz., Hrsg.), Am. Assoc. for Clin. Chem., Washington D.C., 477–494.

(11) Rodgers, R. P. C. (1984): Data analysis and quality control of assays: a practical primer, in: Practical Immunoassay, the state of the art (Butt, W. R. Hrsg.), Dekker-Verlag, New York, 253–308.

(12) Stocker, J. W. et al. (1982): Generation of 2 new mouse myeloma cell lines "PAI" and "PAI-O" for hybridoma production. Hoffmann-La Roche Research Disclosure, 21713, 155–157.

(13) Tijssen, P. (1985): Practice and Theory of Enzyme Immunoassays (Burdon, R. H. & Knippenberg, P. H., Hrsg.), Elsevier, Oxford, UK.

(14) Van Emon, J. M. & Mumma, R. O. Hrsg., (1990): Immunochemical Methods for Environmental Analysis. ACS symposium series 442, ACS Washington, USA.

(15) Wing, K. D., Hammock, B. D. & Wustner, D. A. (1978): Development of an SBioallethrin specific antibody, J. Agric. Food chem., 26, 1328–1333.

(16) Lindl, T. and J. Bauer (Editors): Zell- und Gewebekultur. Einführung in die Grundlagen sowie ausgewählte Methoden und Anwendungen. (Cell and tissue Culture. Introduction to the Principles and Selected Methods and Applications.) Gustau Fischer Verlag, Stuttgart, FRG, 1989.

(17) Martlbauer, E., and G. Terplan: An enzyme-immunological detection of chloramphenicol in milk. Archiv f. Lebensmittelhygiene, Vol. 38, pp. 1–7, 1987.

(18) Naumann, K.: Chemistry of the Synthetic Pyrethroid Insecticides. Vol. 7. In: Wegler, R. (Editor) Chemie der Pflanzenschutz-und Schädlingsbekämpfungsmittel. (chemistry of Plant Protection Agents and Pesticides.) Springer Verlag, Berlin-Heidelberg, FRG, 1981.

(19) Peters, J. H. and H. Baumgarten (Editors): Monoklonale Antikörper: Herstel-lung und Charakterisierung. (Monoclonal Antibodies: Production and Characterization.) Springer-Verlag, Berlin, FRG, 1990.

PATENT PUBLICATIONS

PCT WO 90/10450: Monoclonal Antibodies to Synthetic Pyrethroids and Method for Detecting the Same.

European Patent No. 235,000 A1: Iodine-Marked Pyrethroids, Process and Intermediates for their Preparation, and their Application to Radioimmunoassays.

European Patent No. 365.81 8 A1: Immunological Detection of Atrazine and Atrazine Derivatives.

German Patent Application No. P 4,229,591.2: Immunological Method for the Determination of an Analyte.

We claim:

1. Monoclonal antibodies able to selectively bind to insecticidally or pesticidally active pyrethrins, pyrethroids and their derivatives, the monoclonal antibodies prepared from immunogens which have as a hapten component (1R, cis)-permethrin, (1,R-trans)-permethrin, (1R, cis)-permethric acid, (1, R-trans)-permethric acid or 3-phenoxybenzoic acid.

2. Monoclonal antibodies according to claim 1 directed against a substance selected from the group consisting of pyrethrum, permethrin and phenothrin.

3. Monoclonal antibodies according to claim 1 which are able to selectively bind to cyclopropanecarboxylic acid.

4. Monoclonal antibodies able to selectively bind to insecticidally or pesticidally active pyrethrins, pyrethroids and their derivatives, the monoclonal antibodies prepared from immunogens which have as a hapten component (1R, cis)-permethrin, (1, R-trans)-permethrin, (1R, cis)-permethric acid, (1, R-trans)-permethric acid or 3-phenoxybenzoic acid.

5. Hybridomas secreting monoclonal antibodies of claim 1.

6. Hybridomas secreting monoclonal antibodies of claim 4.

7. A method for producing monoclonal antibodies which are able to selectively bind to insecticidally or pesticidally active pyrethrins, pyrethroids and their derivatives, the monoclonal antibodies prepared from immunogens which have as a hapten component (1,R-cis)-permethrin, (1,R-trans)-permethrin, (1R, cis)-permethric acid, (1,R-trans)-permethric acid or 3-phenoxybenzoic acid, wherein the insecticidally or pesticidally active pyrethrin, pyrethroid or their derivative comprises a phenoxybenzyl and/or a cyclopropane component, the method comprising the steps of:

(a) selecting the hapten and binding the hapten to a protein carrier to produce a synthesized immunoconjugate;

(b) immunizing a donor animal with the synthesized immunoconjugate;

(c) isolating immunocompetent B-lymphocytes from the donor animal;

(d) fusing the B-lymphocytes with a myeloma cell to form hybridoma cells;

(e) cloning the hybridoma cells;

(f) screening the hybridoma cells to isolate hybridoma cells which secrete an antibody capable of selectively binding to the substance; and (g) cultivating the isolated hybridoma cells from step (f) in vivo or in vitro to produce and subsequently isolate the monoclonal antibodies.

8. A method according to claim 7 additionally comprising the step of selecting the hapten to be a permethric acid (1R,cis/1R,trans) or 3-phenoxybenzoic acid.

9. A method according to claim 7 wherein the pyrethrins are selected to be compounds with the structure:

where R1 is $CH_3$ or $CO_2CH_3$; and where R2 is H, $CH_3$, $CH_2CH_3$, or $CHCH_2$.

10. A method according to claim 7 wherein the hybridoma cells are selected from cells deposited under deposit numbers DSM ACC 2135 and DSM ACC 2136 at the International Depository DSM.

11. A method for detecting the presence of an analyte in a sample, the analyte comprising an insecticidal or pesticidal active substance as defined in claim 1 by a displacement immunoassay using monoclonal antibodies as defined in claim 1, the method comprising the steps of:

(a) applying the antibodies to a carrier membrane comprised of a porous or absorbable material and adding a biotin tracer;

(b) dissolving the sample to form a solution;

(c) dipping the membrane into the solution, wherein the solution additionally comprises an avidin enzyme conjugate;

(d) permitting the solution to migrate by capillary action through the membrane and the antibodies thereon to cause a displacement between the biotin tracer and the analyte on the membrane immobilized antibodies;

(e) washing the membrane;

(f) dipping the membrane into a buffered substrate solution specific for the enzyme to produce a color change proportional to the amount of analyte present.

12. A method according to claim 11 wherein the pyrethrins are selected to be compounds with the structure:

where R1 is $CH_3$ or $CO_2CH_3$; and where $R_2$ is H, $CH_3$, $CH_2CH_3$, or $CHCH_2$.

13. The method of claim 12 wherein the monoclonal antibody used is defined in claim 2.

14. The method of claim 11 wherein the monoclonal antibody used is defined in claim 3.

15. A kit for detecting the presence of an analyte in a sample, the analyte defined in claim 1 by a displacement immunoassay, the kit comprising:

(a) a solution of monoclonal antibodies as defined in claim 1, the antibodies being affixed or immobilized on a porous or absorbable material or membrane; a solution additionally comprising an avidin (streptavidin) enzyme conjugate;

(b) a carrier membrane which permits a solution applied thereto to migrate by capillary action through the membrane and the affixed/immobilized antibodies thereon;

(c) a buffered substrate solution specific for the enzyme which will produce a color change proportional to the amount of analyte present.

16. The kit of claim 15 wherein the antibodies are defined in claim 2.

17. The kit of claim 15 wherein the antibodies are defined in claim 3.

18. A test kit comprising the monoclonal antibodies of claim 1 for detecting substances as defined in claim 1.

* * * * *